United States Patent [19]

Whitcomb

[11] Patent Number: 5,047,566

[45] Date of Patent: Sep. 10, 1991

[54] COLORLESS FERRIC ALKYLPHOSPHATES

[75] Inventor: David R. Whitcomb, Maplewood, Minn.

[73] Assignee: Minnesota Mining and Manufacturing Company, St. Paul, Minn.

[21] Appl. No.: 73,890

[22] Filed: Jul. 7, 1987

Related U.S. Application Data

[63] Continuation-in-part of Ser. No. 896,766, Aug. 14, 1986, abandoned.

[51] Int. Cl.$^5$ .................... C07F 9/141; C07F 15/02
[52] U.S. Cl. ........................................ 556/24
[58] Field of Search .......................... 556/24

[56] References Cited

U.S. PATENT DOCUMENTS

| | | | |
|---|---|---|---|
| 2,777,874 | 1/1957 | Asseff et al. | 556/24 X |
| 3,483,143 | 12/1969 | King et al. | 556/24 X |
| 3,491,133 | 1/1970 | Revukas | 556/24 |
| 3,987,145 | 10/1976 | Bruns et al. | 556/24 X |
| 4,049,612 | 9/1977 | Sandler | 556/24 X |
| 4,111,839 | 9/1978 | Meyer | 556/24 X |
| 4,533,930 | 8/1985 | Shioi et al. | 556/24 X |

OTHER PUBLICATIONS

"Chemical Abstracts", 76, 159005w (1972).

"Chemical Abstracts", 96, 154383w (1982).

J. Inorg. Nucl. Chem., 1968, vol. 30, pp. 1553–1561, "The Infra-Red Spectra of Complexes of Beryllium with Tri-n-octylphosphine Oxide and Di(2-ethylhexyl) Phosphoric Acid", L. E. Smythe, T. L. Whateley and R. L. Werner.

*Primary Examiner*—Paul F. Shaver
*Attorney, Agent, or Firm*—Gary L. Griswold; Walter N. Kirn; Mark A. Litman

[57] ABSTRACT

There is disclosed novel colorless ferric di-alkylphosphates of the general formula $$Fe[OOP(OR)_2]_3 \cdot X$$

or $$Fe[OOP(OR)_2]_3$$

in which each R is independently a branched chain alkyl group and X is an anion selected from $F^-$, $PF_6^-$, $BF_4^-$, $Ph_4B^-$, $CH_3COO^-$, $C_2H_5COO^-$, $C_{14}H_{29}SO_4^-$. These compounds react with chelates to give intense and dark colored results and find utility in thermographic materials.

11 Claims, No Drawings

COLORLESS FERRIC ALKYLPHOSPHATES

This is a continuation-in-part of application Ser. No. 896,766 filed Aug. 14, 1986, now abandoned.

BACKGROUND OF THE INVENTION

1. Field of the Invention

The invention relates to novel colorless ferric alkylphosphates which are useful in thermographic materials. At elevated temperatures these ferric alkylphosphates react with a range of colorless chelates (e.g., catechols, β-diketones, o-hydroxynaphthamides, derivatives of salicylic acid) to give intense dark images. The thermographic materials are stable at room temperatures.

2. Background of the Art

For many years heat-sensitive imaging sheets have been used for copying, thermal printing, thermal recording, and thermal labeling. Many of these materials involve thermally increasing the reactivity of two or more components of a color forming reaction which do not react substantially at normal room temperatures. One commonly used reaction system involves a ligand or chelate and a transition metal salt which on thermal stimulation react to form a complex exhibiting an intense and stable color (e.g., U.S. Pat. No. 2,663,654). Transition metals used include iron, nickel, and cobalt and the salts formed are frequently of organic acids such as long-chain carboxylic acids and aromatic acids such as naphthalic acid (e.g., U.S. Pat. Nos. 3,094,620; 3,293,055; 3,953,659). Ferric iron is probably the most preferred transition metal (U.S. Pat. No. 4,531,141) because of its intense near black images and its controllable reactivity with ligands and chelates.

However, many of the ferric salts of organic acids are heavily colored in themselves and most have some objectionable level of coloration. It has been of considerable interest, as evidenced in the published art, to reduce the colored background tint in thermographic materials and sheets (U.S. Pat. Nos. 3,953,659; 4,531,141). These latter approaches include efforts to mask the inherent color tint of the ferric salt by the addition of white filler materials or by modifying the optical properties of the layer surface.

Amongst the many heavy metal salts of organic acids which have been disclosed as reacting with ligands and chelates to give a visible image, a number are colorless (U.S. Pat. No. 3,111,423; 3,293,055). The metals involved, such as zinc and aluminum, must however be reacted with ligands or chelates which contribute the color and indeed have a color cast before reaction. The reacted color is not very intense in most cases.

Organic phosphorus-iron compounds are known in the art which are substantially colorless. U.S. Pat. No. 4,049,612 discloses colorless ferric salts of organo-phosphinic acids which, however, have high melting points (greater than 300° C.) and as a result have low reactivity at typical thermal imaging temperatures. In U.S. Pat. No. 3,483,143 ferric salts of organo-phosphinic and organo-phosphoric acids are disclosed as components of inorganic polymer systems with high structural strength and high melting points (greater than 400° C.). Smythe et al. in J. Inorg. Nucl. Chem., vol. 30, pages 1553–1561 (1968), discuss the infrared spectra of ferric di(2-ethylhexyl)phosphate. In U.S. Pat. No. 4,533,930 ferric salts of organo-phosphoric and other phosphorus acids are disclosed as being near colorless and suitable for thermographic reactions and imaging processes. The preferred salts of that patent involve the addition of a carboxylic acid in the formation of the salt which is said to give a "composite iron salt".

The present invention identifies novel ferric di-alkylphosphates which are truly colorless, have melting points between 50° C. and 300° C., and react with ligands or chelates to give intense dark colors under the influence of heat.

SUMMARY OF THE INVENTION

The invention provides novel colorless ferric dialkylphosphates of the form

$$Fe[OOP(OR)_2]_3 \cdot X \qquad (I)$$

and

$$Fe[OOP(OR)_2]_3 \qquad (II)$$

in which R is a branched chain alkyl group and X is an anion different from the phosphate ion.

These ferric salts are colorless and stable at room temperatures. They react readily at elevated temperatures with chelates such as mono-, bis-, and poly-catechols. They react at lower temperatures with some catechols and ligands. They exhibit endotherms at relatively low temperatures (less than 350° C. and preferably less than 250° C.) which facilitates their reaction with chelates at elevated temperatures.

These salts find utility in thermographic materials where there is a requirement for a truly colorless background. They are also of value in pressure activated printing papers such as carbonless typing paper.

DETAILED DESCRIPTION OF THE INVENTION

The present invention requires the use of substantially colorless ferric dialkylphosphates. The term colorless indicates that the material displays an optical density of less than 0.2 at any point between 410 and 700 nm. These compounds are both stable within the imaging system and capable of forming high optical density images upon reaction with complexing agents.

Composite iron salts containing a total of three anions per Fe(III) ion chosen from dialkylphosphates and carboxylates are disclosed in U.S. Pat. No. 4,533,930. Their disclosed preparation methods however do not allow of the production of complexes of the form

$$Fe[OOP(OR)_2]_3 \cdot X \qquad (I)$$

where R is a branched chain alkyl and X is an anion different from the phosphate ion. Their disclosed preparation methods also give only colored forms of complexes of the form

$$Fe[OOP(OR)_2]_3 \qquad (II)$$

where R is as above.

This invention therefore teaches novel ferric salts of the form (I) or (II), in which each R is selected independently from the group represented by the formula

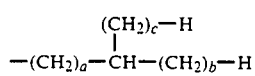
$$-(CH_2)_a-\underset{\underset{H}{|}}{\overset{(CH_2)_c-H}{C}}-(CH_2)_b-H$$

in which $b>a$, $b>c$, c is 1 through 10,
and $3<=a+b<=18$
and X is a singly charged anion selected from non-metallic anions. Preferred anions for X are $F^-$, $PF_6^-$, $Ph_4B^-$, $BF_4^-$, $CH_3COO^-$, $C_2H_5COO^-$, $C_{14}H_{29}SO_4^-$.

The iron complexes of this invention are truly uncolored and find utility in thermographic materials and in carbonless carbon papers. They react with colorless chelates such as catechols to form dark near-black images. With heavily ballasted catechols, and with bis-catechols and polycatechols showing no electronic interaction between the individual catechols, these iron complexes react rapidly at elevated temperatures (e.g., above 60° C.) but are unreactive at room temperatures. With simple catechols they react at room temperatures. With $\beta$-diketones, o-hydroxynaphthamides, or derivatives of salicylic acid, or colorless chelates reaction occurs at elevated temperatures to give brown or purple images.

Dialkylorganophosphates are the preferred ligand for the iron(III) in the practice of the present invention since the resulting complexes are completely colorless. Mixed dialkylphosphate/carboxylate iron complexes as disclosed in U.S. Pat. No. 4,533,930 can be made to be less colored but they still retain undesirable color because of the presence of the carboxylate. The iron complexes of the sulfur analogues of the carboxylates, phosphates, and their mixtures (also in U.S. Pat. No. 4,533,930) are particularly undesirable since highly colored, even black, materials are produced.

If trialkylphosphates are used as the main ligand, sufficiently stable iron complexes do not form, and if monoalkylphosphates (as well as inorganic phosphates) are used, generally undesirable, extensive crosslinking occurs between metal centers such that the resulting iron organophosphate is too stable to react with chelates such as catechol. Aromatic organophosphates often provide an iron complex that is high melting, less reactive and more colored than the dialkylphosphates.

The most preferred organophosphate ligands are branched chain dialkylphosphates, and especially di-2-ethylhexylphosphate (DEHP). Linear chain dialkylphosphates form colorless iron complexes that give images with catechols but are generally too unreactive (too highly crosslinked) to provide sufficient image density. The branch on the main chain should be sufficiently long and sufficiently close to the metal center that crosslinking between metal centers is inhibited. On the other hand, the branch should not be too long or too close to the phosphorus center since iron that is incompletely reacted with the phosphate may result in a colored iron source, and would probably be too reactive in the coating solution. From a practical aspect, the ideal is illustrated with DEHP. The range for the side chain length might be best put at about 1-10 carbons, the further from the connection point to the phosphorus the longer the required chain. The length of the main chain is best illustrated by DEHP, that is, around 6-10 carbons. Chains as long as 18 carbons is the practical maximum due to the required loading necessary to achieve suitable optical density (i.e., molecular weight becomes impractically high).

Asymmetric dialkylphosphates would be expected to provide a lower melting iron complex. DEHP not only works well, it is commercially available in large quantities of relatively good purity.

Fe(DEHP)$_3$ is preferred in the iron organophosphate series. It is completely colorless, a major improvement over the iron carboxylates and mixed carboxylate/organophosphate iron complexes. In addition, unlike the general straight chain dialkylphosphate iron complexes, it is very thermally reactive with the bis-catechols. It is also insoluble in the organic solvents required to coat this type of thermal imaging construction, unlike the mixed carboxylate/organophosphate iron complexes disclosed in U.S. Pat. No. 4,533,930.

In the preparation of Fe(DEHP)$_3$ we found a difference between using ferric nitrate as the source of iron(III) and the ferric chloride or ferric sulfate as disclosed in the literature. Our preferred source of iron(III) is the nitrate since the other salts impart a yellow color to the iron organophosphate complex. In the case of the chloride this appears to be due to Fe-Cl-Fe linkages. Iron organophosphate complexes free of chloride in amounts sufficient to impart yellow tones to the complex are preferred.

Reported in the literature (Smythe et al. in Example A, hereinafter referenced) is the aqueous preparation of Fe(DEHP)$_3$ from a stoichiometric amount of NaDEHP in solution added to a solution of ferric sulfate. One could expect that the Fe-OH species would be obtained under these conditions leading to undesirable color in the complex. A pale yellow complex was in fact obtained, with reasonably good solubility in cyclohexane (some fine colloidal solid remaining) and a main endotherm in the differential scanning calorimeter (DSC) of 299° C.

On the other hand in Example A1, the use of ferric nitrate gives an improved whiteness to the product. In addition, carefully changed conditions of aqueous preparation described in Example A2 produce a completely colorless form of Fe(DEHP)$_3$ which is rubbery and insoluble in cyclohexane.

This preferred method of making Fe(DEHP)$_3$ uses an alkali metal salt of DEHP rather than the acid itself which is of low solubility in water. The DEHP$^-$K$^+$ is made in situ in aqueous solution and added to aqueous ferric nitrate. Alkali hydrolysis of P-O-C linkages is known and in order to prevent formation of a monoalkylphosphate from the dialkylphosphate, two steps were taken. First, potassium hydroxide was used as a base since it can be added to water rapidly with minimal heat buildup, unlike sodium hydroxide. Second, the DEHP is added rapidly to the KOH solution which is then added rapidly to the Fe(III) solution. The latter is initially a light yellow (darker with increasing iron concentrations) from hydrolysis of the Fe(III) form, —initially, oligomeric Fe-OH species. Left to its own devices it will eventually form insoluble polymeric iron hydroxides that would be too inert to react with organophosphates. Therefore, the Fe(III) solution is prepared immediately prior to use, and the color of the solution rapidly diminishes as the DEHP$^-$K$^+$ solution is added. A white, rubbery solid results which is easily separated from the colorless filtrate. In contrast to the Smythe et al. report this product is only poorly soluble in cyclohexane.

Because of the change in color, texture, and solubility in cyclohexane we believe the product of the above making conditions is novel and is truly Fe(DEHP)$_3$ whereas the previously reported materials are some form of composite.

Similar aqueous preparation methods were successful in making composite salts of the form of formula I.

where X was F$^-$, PF$_6^-$, BF$_4^-$, Ph$_4$B$^-$, and C$_{14}$H$_{29}$SO$_4^-$. These materials were all found to be colorless.

However the aqueous preparation when used with an added acetate ion gave neither the composite of the formula I nor the composites of the type disclosed by U.S. Pat. No. 4,533,930 {Fe(DEHP)$_x$(OOCH$_3$)$_y$ where x+y=3}; the preparations did in fact give materials of the formula II i.e., Fe(DEHP)$_3$. We believe that the acetate ion is too soluble in water to remain in the complex form. We did find that reacting ferric nitrate with DEHP acid in correct proportions in glacial acetic acid gave a colorless material of the form of formula II with X=CH$_3$COO$^-$. Purification was accomplished by inducing precipitation from cyclohexane, in which the material is very soluble, by addition of acetone (see Example B). Attempts to make other carboxylate equivalents by this technique were not successful; using glacial propionic, or methacrylic acids as solvent the reaction appears to proceed but no solid precipitate occurred.

Furthermore, use of other alkylphosphates where the alkyl, R, was straight chain gave only Fe(OOP(OR)$_2$)$_3$. This was found in examples where R=methyl, n-butyl, n-decyl, n-lauryl, and stearyl. The following are examples of preparative methods for the materials of this invention.

EXAMPLE A

Preparation of Fe(DEHP)$_3$

1. The method is similar to the literature preparation of L. E. Smythe, T. L. Whateley and R. L. Werner (J. Inorg. Nucl. Chem., 30 (1968) 1553) using ferric nitrate in place of ferric sulfate. To 2.0 g KOH in 175.0 ml H$_2$O was added 10.0 g DEHP. This solution is added over 5 minutes to 35.0 ml of water containing 4.0 g Fe(NO$_3$)$_3$.9H$_2$O with vigorous stirring. The mixture was stirred 10 minutes, filtered, washed in fresh water with stirring, filtered and dried under vacuum at 70° C. to a constant weight. An off white solid was obtained. The infrared spectrum shows the expected phosphate stretches, as well as small amounts of OH, and the characteristic ethyl group presence at 1466.1 cm$^{-1}$. The DSC revealed a melting point endotherm of this complex at 120° C.

2. To 1.0 liter of water was added 16.8 g KOH. In a separate 1.5 liters of water was dissolved 11.0 g NaBF$_4$, and then 38.2 g Fe(NO$_3$)$_{3pb}$.9H$_2$O. While the iron salt was dissolving, 97.7 g DEHP was added to the rapidly stirred KOH solution. The thick phosphate solution was added rapidly to the iron solution with mechanical stirring. The pure white, rubbery solid was filtered, washed with stirring, filtered and dried. It was found to be important that the source of iron(III) not be ferric chloride as it gives a yellow product. DSC showed a melting point endotherm of the material to be 145° C. The infrared spectrum of a vacuum dried (room temperature) sample revealed the expected phosphates stretches, but unlike 1 (above) there was no presence of OH.

3. Example A1. was also carried out at elevated temperatures (60° C.) with no disadvantageous effects. The same endotherm (via DSC) was obtained.

EXAMPLE B

Preparation of Fe(DEHP)$_3$(acetate)

Powdered Fe(NO$_3$)$_3$.9H$_2$O, 80.8 g, was dissolved in 800 ml glacial acetic acid. As soon as a clear solution is obtained, 193.0 g bis-(2-ethylhexyl)phosphate was added in a rapid dropwise manner with vigorous stirring. Less than a stoichiometric amount of DEHP gave a more colored product; an excess of DEHP was not disadvantageous. The white product was filtered, washed with acetic acid and dried under vacuum. The approximate yield was 84%. The product was rubbery and could be recrystallized by precipitation from cyclohexaane by acetone. It was important that FeCl$_3$ not be used since a clear yellow acetic acid solution resulted.

Alternative preparation from ethanol

To 40 ml of absolute ethanol was added 2.0 g Fe(NO$_3$)$_3$.9H$_2$O. Upon dissolution, 5.0 g DEHP are added, and the clear solution stirred 5 minutes. An aqueous solution of potassium acetate (0.5 g in 4.5 g H$_2$O) was added dropwise. The mixture was stirred 2 minutes, filtered, redispersed in water, stirred an additional 20 minutes, filtered and vacuum dried. The infrared spectrum was identical to that prepared from acetic acid.

Characterization: The infrared spectrum clearly shows the coordinated organophosphate (1000-1200 cm-1) and carboxylate (1551.0 cm-1 asymmetric stretch, the symmetric stretch is under other peaks), and the absence of Fe-O-Fe stretches. DSC shows a small exotherm centered around 215° C. followed by the main endotherm centered at 282° C. Impure materials generally showed extensive exotherms in place of the endotherm. The complex was readily soluble in cyclohexane, and was an excellent film forming material when coated on a substrate, forming a clear, colorless film. Elemental analysis was consistent with the presence of one carboxylate, and confirmed the 3:1 P:Fe ratio. Magnetic susceptibility determined by the Evan's NMR method (J. Chem. Soc., 1959, 2003) demonstrateed a high spin iron complex. The complex was also found to be conductive in cyclohexane solution.

EXAMPLE C

Preparation of Fe(DEHP)$_3$F

1. To 500.0 g H$_2$O was added 6.0 g KOH. To a separate 500.0 g H2O was added 12.0 g Fe(NO$_3$)$_3$.9H$_2$O followed by 0.62 g NaF. To the aqueous base solution was added 32.0 g DEHP, which was then added rapidly to the mechanically stirred iron solution. The pure white iron complex was filtered, washed and vacuum dried.

2. To 300 ml ethanol was added 16.13 g Fe(NO$_3$)$_3$.9H$_2$O. Upon dissolution, 40.0 g DEHP was added rapidly dropwise (3 minutes). The clear solution was stirred 5 minutes then 3.2 g NaF in 32 g H$_2$O was added dropwise (5 minutes). The white solid was stirred, then diluted with 400 ml H$_2$O, stirred 30 minutes and filtered. A colorless solid resulted. Elemental analysis was consistent with a 3:1:1 P:Fe:F ratio.

EXAMPLE D

Preparation of Fe(DEHP)$_3$(tetradecylsulfate)

A mixture of 1.06 g tetradecylsulfate in 100 g H$_2$O with 1.2 g Fe(NO$_3$)$_3$.9H$_2$O yielded an orange precipitate which was immediately treated with 3.2 g DEHP and 0.6 g KOH in 50 ml H$_2$O. After stirring 3 days a white solid was filtered and air dried. The infrared spectrum was consistent with the proposed material.

EXAMPLE E

Preparation of Fe(DEHP)$_3$(tetraphenylborate)

To 1.1 g sodium tetraphenylborate and 1.0 g Fe(NO$_3$)$_3$.9H$_2$O in 40 ml H$_2$O is added rapidly 3.2 g DEHP and 0.73 g KOH in 80 ml H$_2$O. The mixture was filtered, dispersed in water, stirred, filtered and air dried. The infrared spectrum was consistent with the proposed material.

EXAMPLE F

Preparation of Fe(DEHP)$_3$(Fe(CN)$_6$)

This material illustrates that the choice of the added ion in the complex is important in the final color of the material.

To 25.0 g H$_2$O was added 0.61 g KOH, 3.2 g DEHP and then 1.2 g K$_4$(Fe(CN)$_6$). 3H$_2$O. A total of 1.2 g Fe(NO$_3$)$_3$.9H$_2$O were added, and the mixture shaken over 6 days. A brown solid resulted which was filtered and dried. It exhibited an infrared spectrum that shows the presence of the phosphate and the Fe(CN)$_6$ groups.

The following examples show the use of these materials in thermal imaging applications.

EXAMPLE 1

Thermographic sheet and image using compound of formula II.

A dispersion of the iron tris(di-2-ethylhexyl)phosphate (1) was formed by ball milling for 24 hours 25 g of (1) in 75 g of acetone using flint glass marbles. To 4.0 g of this dispersion was added 3.27 g of 15% ethylacrylate methylmethacrylate copolymer resin in acetone and 0.5 g of the 1,1'-spirobi[-1H-indene]-5,5',6,6'-tetrol-2,2',3,3'-tetrahydro-3,3,3',3'-tetramethyl (2). This was agitated until (2) was dissolved and was then coated on 2 mil opaque titanium dioxide filled polyester at 2.5 mil orifice using a knife coater and allowed to air dry. The resulting thermal recording sheet exhibited excellent whiteness giving a blue image when thermally addressed.

EXAMPLE 2

Thermographic sheet using compound of formula I (acetate).

A dispersion of 25 g of iron tris(di-2-ethylhexyl)phosphate acetate was made with 48.75 g of acetone and 1.25 g of cellulose acetate by ball milling with flint glass balls for 24 hours. A coating dispersion was prepared from 6.0 g of this dispersion, 5 g of a 12% solution of cellulose acetate in acetone, and 9.0 g of a 10% solution of 1,1,-spiro-bi[-H-indene]-5,5',6,6,-tetrol-2,2'',3,3'-tetrahydro-3,3,3',3'-tetramethyl (2)in acetone, coated at 2 mil. wet thickness on 46#(24"×36"×500")paper, and air dried. This thermal recording sheet gave a blue image changing to green within 4 hours. Bkgd=0.16, ID=0.52, Initiation temperature=152° C.

I claim:

1. A colorless iron compound substantially free of carboxylate capable of reacting with a chelate to give a colored iron complex, said iron compound being selected from those represented by the general formulae $$Fe[OOP(OR)_2]_3 \cdot X$$

and

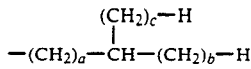

where each R is independently chosen from branched chain alkyl group whose main chain has from 3 to 18 carbon atoms, and X is an anion different from phosphate and wherein compounds of the second formula are insoluble in cyclohexane.

2. A colorless iron compound according to claim 1 wherein R is represented by the general formula $$-(CH_2)_a-CH\begin{array}{c}(CH_2)_c-H\\|\\\end{array}-(CH_2)_b-H$$

in which $b>a$, $b>c$, $c \leq 10$, and $3 \leq a+b \leq 18$, and wherein X is chosen from F$^-$, PF$_6^-$, BF$_4^-$, Ph$_4$B$^-$, CH$_3$COO$^-$, C$_2$H$_5$COO$^-$, and C$_{14}$H$_{29}$SO$_4^-$.

3. A colorless iron compound which is insoluble in cyclohexane of the general formula $$Fe[OOP(OR)_2]_3$$

as recited in claim 1 which is made by the rapid mixing of stoichiometric amounts of an aqueous solution of ferric nitrate and an aqueous solution of an alkali metal salt of a dialkylphosphate of the form $$M[OOP(OR)_2]$$

wherein M is sodium or potassium and each R is independently selected from branched chain alkyl groups whose main chain has from 3 to 18 carbon atoms.

4. The compound of claim 1 selected from the group consisting of ferric di-2-ethylhexylphosphate and a salt of ferric di-2-ethylhexylphosphate.

5. A compound according to claim 3 which is a salt of ferric di-2-ethylhexylphosphate.

6. A compound according to claim 1 which is ferric di-2-ethylhexylphosphate.

7. A compound according to claim 2 which is a salt of ferric di-2-ethylhexylphosphate.

8. A colorless iron compound substantially free of carboxylate capable of reacting with a chelate to give a colored iron complex, said iron compound being selected from those represented by the general formulae $$Fe[OOP(OR)_2]_3 \cdot X$$

and $$Fe[OOP(OR)_2]_3$$

where each R is independently chosen from branched chain alkyl group whose main chain has from 3 to 18 carbon atoms, and X is an anion different from phosphate.

9. A colorless iron compound capable of reacting with a chelate to give a colored iron complex, said iron compound being selected from those represented by the general formulae $$Fe[OOP(OR)_2]_3 \cdot X$$

and $$Fe[OOP(OR_2)]_3$$

where each R is independently chosen from branched chain alkyl group whose main chain has from 3 to b 18 carbon atoms, and X is an anion different from phosphate.

10. A colorless iron compound of the general formula

Fe[OOP(OR)$_2$]$_3$ as recited in claim 8 which is made by the rapid mixing of stoichiometric amounts of an aqueous solution of ferric nitrate and an aqueous solution of an alkali metal salt of a dialkylphosphate of the form

M[OOP(OR)$_2$]

where M is sodium or potassium and R is as defined above.

11. A colorless iron compound of the general formula

Fe[OOP(OR)$_2$]$_3$ as recited in claim 9 which is made by the rapid mixing of stoichiometric amounts of an aqueous solution of ferric nitrate and an aqueous solution of an alkali metal salt of a dialkylphosphate of the form

M[OOP(OR)$_2$]

where M is sodium or potassium and R is as defined above.

* * * * *

UNITED STATES PATENT AND TRADEMARK OFFICE
CERTIFICATE OF CORRECTION

PATENT NO. : 5,047,566

DATED : September 10, 1991

INVENTOR(S) : David R. Whitcomb

It is certified that error appears in the above-identified patent and that said Letters Patent is hereby corrected as shown below:

Column 3, line 5: Delete "$CH_3COO-$, $C_2H_5COO-$" and substitute --$NO_3-$ --;

Column 5, line 14: "X=$CH_3COO-$" should read --$NO_3-$ --;
Column 5, lines 17-21: Delete "Attempts . . . cured."
Column 5, line 66: "(acetate)" should read --($NO_3$)- --;
Column 6, line 24: "carboxylate" should read --nitrate--;
Column 6, line 35: "carboxylate" should read --nitrate--;
Column 6, line 37: "demonstrateed" should read --demonstrated--;
Column 7, line 46: "(acetate)" should read --(nitrate)--;
Column 8, line 1: "$Fe[OOP(OR)_2]_3$" should be preceded by --and--;

UNITED STATES PATENT AND TRADEMARK OFFICE
CERTIFICATE OF CORRECTION

PATENT NO. : 5,047,566

DATED : September 10, 1991

INVENTOR(S) : David R. Whitcomb

It is certified that error appears in the above-identified patent and that said Letters Patent is hereby corrected as shown below:

Claim 2, line 1: Delete "according to claim 1" and insert --substantially free of carboxylate capable of reacting with a chelate to give a colored iron complex, said iron compound being selected from those represented by the general formulae $$Fe[OOP(OR)_2]_3 \cdot X$$
$$\text{and } Fe[OOP(OR)_2]_3$$

where each R is independently chosen from branched chain alkyl group whose main chain has from 3 to 18 carbon atoms, and X is an anion different from phosphate and wherein compounds of the second formula are insoluble in cyclohexane,--

Column 8, line 17: "$CH_3COO-$, $C_2H_5COO-$" should read --$NO^3$--;

UNITED STATES PATENT AND TRADEMARK OFFICE
CERTIFICATE OF CORRECTION

PATENT NO. : 5,047,566

DATED : September 10, 1991

INVENTOR(S) : David R. Whitcomb

It is certified that error appears in the above-identified patent and that said Letters Patent is hereby corrected as shown below:

Column 8,

Claim 5, line 1: Delete "according to claim 3" and insert after "which" --is a colorless iron compound insoluble in cyclohexane of the general formula $$Fe[OOP(OR)_2]_3$$

which is made by the rapid mixing of stoichiometric amounts of an aqueous solution of ferric nitrate and an aqueous solution of an alkali metal salt of a dialkylphosphate of the formula $$M[OOP(OR)_2]$$

where M is sodium or potassium and each R is independently selected from branched chain alkyl groups whose main chain has from 3 to 18 carbon atoms and where in said compound--

Signed and Sealed this

Eighth Day of February, 1994

BRUCE LEHMAN

Attest:

*Attesting Officer*   *Commissioner of Patents and Trademarks*